US008569052B2

(12) United States Patent
Federspiel et al.

(10) Patent No.: US 8,569,052 B2
(45) Date of Patent: Oct. 29, 2013

(54) OXYGEN DEPLETION DEVICES AND METHODS FOR REMOVING OXYGEN FROM RED BLOOD CELLS

(75) Inventors: William J. Federspiel, Pittsburgh, PA (US); Brian J. Frankowski, Imperial, PA (US); Tatsuro Yoshida, West Newton, MA (US); Paul J. Vernucci, Billerica, MA (US)

(73) Assignees: New Health Sciences, Inc., Bethesda, MD (US); University of Pittsburgh-Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 13/115,532

(22) Filed: May 25, 2011

(65) Prior Publication Data

US 2012/0100523 A1    Apr. 26, 2012

Related U.S. Application Data

(63) Continuation of application No. 12/903,057, filed on Oct. 12, 2010, now abandoned.

(60) Provisional application No. 61/250,661, filed on Oct. 12, 2009.

(51) Int. Cl.
*C12N 5/00* (2006.01)

(52) U.S. Cl.
USPC ........................................ 435/325; 435/283.1

(58) Field of Classification Search
USPC ........................................ 435/2, 325, 283.1
See application file for complete search history.

(56) References Cited

U.S. PATENT DOCUMENTS

| | | | |
|---|---|---|---|
| 4,086,924 A | 5/1978 | Latham, Jr. | |
| 4,228,032 A | 10/1980 | Talcott | 252/400 R |
| 4,300,559 A | 11/1981 | Gajewski et al. | 128/272 |
| 4,370,160 A | 1/1983 | Ziemelis | |
| 4,381,775 A | 5/1983 | Nose' et al. | |
| 4,540,416 A | 9/1985 | Hattori et al. | |
| 4,572,899 A | 2/1986 | Walker et al. | |
| 4,585,735 A | 4/1986 | Meryman et al. | |
| 4,654,053 A | 3/1987 | Sievers et al. | |
| 4,670,013 A | 6/1987 | Barnes et al. | |
| 4,701,267 A | 10/1987 | Watanabe et al. | |
| 4,713,176 A | 12/1987 | Schoendorfer et al. | |
| 4,748,121 A | 5/1988 | Beaver et al. | |
| 4,749,551 A | 6/1988 | Borgione | 422/48 |
| 4,769,175 A | 9/1988 | Inoue | |
| 4,769,318 A | 9/1988 | Hamasaki et al. | |
| 4,837,047 A | 6/1989 | Sato et al. | |
| 4,880,548 A | 11/1989 | Pall et al. | |
| 4,880,786 A | 11/1989 | Sasakawa et al. | |
| 4,902,701 A | 2/1990 | Batchelor et al. | |
| 4,925,572 A | 5/1990 | Pall | |
| 5,000,848 A | 3/1991 | Hodgins et al. | |
| 5,023,054 A | 6/1991 | Sato et al. | |
| 5,037,419 A | 8/1991 | Valentine et al. | |
| 5,152,905 A | 10/1992 | Pall et al. | |
| 5,192,320 A | 3/1993 | Anazawa et al. | 623/12 |
| 5,208,335 A | 5/1993 | Ramprasad et al. | |
| 5,229,012 A | 7/1993 | Pall et al. | |
| 5,254,248 A | 10/1993 | Nakamura et al. | |
| 5,353,793 A | 10/1994 | Bornn | |
| 5,356,375 A | 10/1994 | Higley | |
| 5,362,442 A | 11/1994 | Kent | |
| 5,386,014 A | 1/1995 | Nho et al. | |
| 5,387,624 A | 2/1995 | Morita et al. | |
| 5,417,986 A | 5/1995 | Reid et al. | |
| 5,427,663 A | 6/1995 | Austin et al. | |
| 5,443,743 A | 8/1995 | Gsell | |
| 5,476,764 A | 12/1995 | Bitensky | |
| 5,506,141 A | 4/1996 | Weinreb et al. | |
| 5,529,821 A | 6/1996 | Ishikawa et al. | |
| 5,617,873 A | 4/1997 | Yost et al. | |
| 5,624,794 A | 4/1997 | Bitensky et al. | 435/2 |
| 5,635,358 A | 6/1997 | Wilding et al. | |
| 5,691,452 A | 11/1997 | Gawryl et al. | |
| 5,693,230 A | 12/1997 | Asher | |
| 5,698,250 A | 12/1997 | DelDuca et al. | |
| 5,730,989 A | 3/1998 | Wright | |
| 5,750,115 A | 5/1998 | Van Den Bosch | |
| 5,783,094 A | 7/1998 | Kraus et al. | |
| 5,783,148 A | 7/1998 | Cottingham et al. | |

(Continued)

FOREIGN PATENT DOCUMENTS

DE    3722984    1/1989
EP    0 100 419 A2    2/1984

(Continued)

OTHER PUBLICATIONS

International Search Report and Written Opinion dated Apr. 27, 2011 for corresponding International Patent Application No. PCT/US2010/044045.

(Continued)

*Primary Examiner* — Ruth Davis
(74) *Attorney, Agent, or Firm* — Arnold & Porter LLP (57) ABSTRACT

An oxygen depletion device. The device has a cartridge; a plurality of hollow fibers extending within the cartridge from an entrance to an exit thereof; an amount of an oxygen scavenger packed within the cartridge and contiguous to and in between the plurality of hollow fibers. The hollow fibers are adapted to receiving and conveying red blood cells. There is another embodiment of an oxygen depletion device and method for removing oxygen from red blood cells.

17 Claims, 5 Drawing Sheets

(56) References Cited

U.S. PATENT DOCUMENTS

| | | |
|---|---|---|
| 5,789,151 A | 8/1998 | Bitensky et al. |
| 5,811,142 A | 9/1998 | DelDuca et al. |
| 5,846,427 A | 12/1998 | Kessler et al. |
| 5,972,710 A | 10/1999 | Weigl et al. |
| 6,027,623 A | 2/2000 | Ohkawa |
| 6,047,203 A | 4/2000 | Sackner et al. |
| 6,090,062 A | 7/2000 | Sood et al. |
| 6,150,085 A | 11/2000 | Hess et al. |
| 6,162,396 A | 12/2000 | Bitensky et al. ............... 422/44 |
| 6,187,572 B1 | 2/2001 | Platz et al. |
| 6,210,601 B1 | 4/2001 | Hottle et al. |
| 6,231,770 B1 | 5/2001 | Bormann et al. |
| 6,254,628 B1 | 7/2001 | Wallace et al. |
| 6,337,026 B1 | 1/2002 | Lee et al. |
| 6,368,871 B1 | 4/2002 | Christel et al. |
| 6,387,461 B1 | 5/2002 | Ebner et al. |
| 6,403,124 B1 | 6/2002 | Dottori |
| 6,413,713 B1 | 7/2002 | Serebrennikov |
| 6,439,577 B2 | 8/2002 | Jorgensen et al. |
| 6,447,987 B1 | 9/2002 | Hess et al. |
| 6,468,732 B1 | 10/2002 | Malin et al. ..................... 435/2 |
| 6,475,147 B1 | 11/2002 | Yost et al. |
| 6,482,585 B2 | 11/2002 | Dottori |
| 6,527,957 B1 | 3/2003 | Deniega et al. |
| 6,564,207 B1 | 5/2003 | Abdoh |
| 6,610,772 B1 | 8/2003 | Clauberg et al. |
| 6,688,476 B2 | 2/2004 | Breillatt, Jr. et al. |
| 6,695,803 B1 | 2/2004 | Robinson et al. |
| 6,697,667 B1 | 2/2004 | Lee et al. |
| 6,723,051 B2 | 4/2004 | Davidson et al. |
| 6,761,695 B2 | 7/2004 | Yost et al. |
| 6,773,407 B2 | 8/2004 | Yost et al. |
| 6,817,979 B2 | 11/2004 | Nihtilä |
| 6,866,783 B2 * | 3/2005 | Baurmeister et al. ......... 210/649 |
| 6,955,648 B2 | 10/2005 | Mozayeni et al. |
| 7,104,958 B2 | 9/2006 | Crutchfield et al. |
| 7,208,120 B2 | 4/2007 | Bitensky et al. |
| 7,347,887 B2 | 3/2008 | Bulow et al. |
| 7,361,277 B2 | 4/2008 | Bormann et al. |
| 7,431,995 B2 | 10/2008 | Smith et al. |
| 7,452,601 B2 | 11/2008 | Ebner et al. |
| 7,721,898 B2 | 5/2010 | Yagi et al. |
| 7,723,017 B2 | 5/2010 | Bitensky et al. |
| 7,754,798 B2 | 7/2010 | Ebner et al. |
| 7,775,376 B2 | 8/2010 | Bonaguidi et al. |
| 8,071,282 B2 | 12/2011 | Bitensky et al. |
| 2001/0027156 A1 | 10/2001 | Egozy et al. |
| 2002/0062078 A1 | 5/2002 | Crutchfield et al. |
| 2002/0066699 A1 | 6/2002 | Boggs et al. |
| 2002/0085952 A1 | 7/2002 | Ellingboe et al. |
| 2002/0086329 A1 | 7/2002 | Shvets et al. |
| 2002/0099570 A1 | 7/2002 | Knight |
| 2002/0182241 A1 | 12/2002 | Borenstein et al. |
| 2003/0003575 A1 | 1/2003 | Vacanti et al. |
| 2003/0062299 A1 | 4/2003 | Lee et al. |
| 2003/0124504 A1 | 7/2003 | Bitensky et al. |
| 2003/0183801 A1 | 10/2003 | Yang et al. |
| 2003/0189003 A1 | 10/2003 | Kraus et al. |
| 2004/0026341 A1 | 2/2004 | Hogberg et al. |
| 2004/0168982 A1 | 9/2004 | Bitensky et al. |
| 2005/0038342 A1 | 2/2005 | Mozayeni et al. |
| 2005/0137517 A1 | 6/2005 | Blickhan et al. |
| 2005/0139806 A1 | 6/2005 | Havens et al. |
| 2005/0208462 A1 | 9/2005 | Bitensky et al. |
| 2005/0230856 A1 | 10/2005 | Parekh et al. .............. 261/122.1 |
| 2005/0233302 A1 | 10/2005 | Hess et al. |
| 2006/0081524 A1 | 4/2006 | Sengupta et al. |
| 2006/0118479 A1 | 6/2006 | Shevkoplyas et al. |
| 2007/0078113 A1 | 4/2007 | Roth et al. |
| 2007/0240569 A1 | 10/2007 | Ooya |
| 2008/0243045 A1 | 10/2008 | Pasqualini .................. 604/5.04 |
| 2009/0017128 A1 | 1/2009 | Monzyk et al. |
| 2009/0269837 A1 | 10/2009 | Shevkoplyas et al. |
| 2010/0221697 A1 | 9/2010 | Sehgal |
| 2010/0313755 A1 | 12/2010 | Koros et al. |
| 2012/0024156 A1 | 2/2012 | Yoshida et al. |
| 2012/0129148 A1 | 5/2012 | Hess et al. |
| 2012/0219633 A1 | 8/2012 | Sowemimo-Coker |

FOREIGN PATENT DOCUMENTS

| | | |
|---|---|---|
| EP | 0 217 759 A1 | 4/1987 |
| EP | 0 299 381 A2 | 1/1989 |
| EP | 0 890 368 A1 | 1/1999 |
| FR | 2 581 289 A1 | 11/1986 |
| GB | 1 044 649 A2 | 10/1966 |
| JP | 58-194879 | 11/1983 |
| JP | 63-63616 A | 3/1988 |
| JP | 01-104271 A | 4/1989 |
| JP | 5-503075 A | 5/1993 |
| JP | 5-503304 A | 6/1993 |
| JP | 5-305123 A | 11/1993 |
| JP | 06-121920 A | 5/1994 |
| JP | 2700170 B2 | 1/1998 |
| JP | 2000-516963 A | 12/2000 |
| JP | 2002-253936 A | 9/2002 |
| JP | 2005-535279 A | 11/2005 |
| KR | 10-0721054 | 5/2006 |
| SU | 1718766 A1 | 1/1990 |
| WO | WO 81/02239 A1 | 8/1981 |
| WO | WO 86/00809 A1 | 2/1986 |
| WO | WO 89/02274 A1 | 3/1989 |
| WO | WO 91/04659 A1 | 4/1991 |
| WO | WO 92/08348 A1 | 5/1992 |
| WO | WO 95/29662 A2 | 11/1995 |
| WO | WO 96/29864 A1 | 10/1996 |
| WO | WO 99/48963 A2 | 9/1999 |
| WO | WO 03/043571 A2 | 5/2003 |
| WO | WO 2006-057473 A1 | 6/2006 |
| WO | WO 2006/057473 A1 | 6/2006 |
| WO | WO 2011/014855 A2 | 2/2011 |

OTHER PUBLICATIONS

International Search Report and Written Opinion dated Feb. 18, 2011 for corresponding International Patent Application No. PCT/US2010/052084.

International Search Report and Written Opinion dated Dec. 6, 2010 for corresponding International Patent Application No. PCT/US2010/052376.

International Preliminary Report on Patentability Dated May 24, 2012 From Corresponding PCT Application No. PCT/US2010/52376.

Alcantar et al., "Polyethylene glycol-coated biocompatible surfaces," *Journal of Biomedical Materials Research*, 51(3):343-351 (2000).

Anderson et al., "Microfabrication and microfluidics for tissue engineering: state of the art and future opportunities," *Lab Chip*, 4:98-103 (2004).

Barbee et al., "The Fahraeus Effect," *Microvascular Research*, 3:6-16 (1971).

Barclay et al., "A Method for Detecting Chaos in Canine Myocardial Microcirculatory Red Cell Flux," *Microcirculation*, 7(5):335-346 (2000).

Bardy et al., "Technetium-99m Labeling by Means of Stannous Pyrophosphate: Application to Bleomycin and Red Blood Cells," *Journal of Nuclear Medicine*, 16(5):435-437 (1975).

Barras et al., "Einfluss der Rejuvenation auf die rheologischen Eigenschaften gelagerter Erythrozyten," *VASA*, 23(4):305-311 (1994).

Beutler et al., "Storage of red cell concentrates in CPD-A2 for 42 and 49 days," *The Journal of Laboratory and Clinical Medicine*, 102(1):53-62 (1983).

Borenstein et al., "Microfabrication Technology for Vascularized Tissue Engineering," *Biomedical Microdevices*, 4(3):167-175 (2002).

Brody et al., "Deformation and Flow of Red Blood Cells in a Synthetic Lattice: Evidence for an Active Cytoskeleton," *Biophysical Journal*, 68:2224-2232 (1995).

Carmen, "The Selection of Plastic Materials for Blood Bags," *Transfusion Medicine Reviews*, 7(1):1-10 (1993).

(56) References Cited

OTHER PUBLICATIONS

Carr et al., "Nonlinear Dynamics of Microvascular Blood Flow," *Annals of Biomedical Engineering*, 28:641-652 (2000).
Cell Deformability, RheoSCAN (RheoScan-AnD300/RheoScan-D300), obtained on Dec. 11, 2012, from: http://www.rheoscan.com/products/products/products-01.html.
Chilton et al., "Privacy Protection of Health Information: Patient Rights and Pediatrician Responsibilities," *Pediatrics*, 104(4):973-977 (1999).
Cokelet et al., "Fabrication of in Vitro Microvascular Blood Flow Systems by Photolithography," *Microvascular Research*, 46:394-400 (1993).
Dale et al., "Human Vaccination with *Escherichia coli* J5 Mutant Induces Cross-Reactive Bactericidal Antibody against *Neisseria gonorrhoeae* Lipooligosaccharide," *The Journal of Infectious Diseases*, 166:316-325 (1992).
De Angelis et al., "Erythrocyte Shape Control in Stored Blood: The Effect of Additive Solutions on Shape Recovery," *Haematologica*, 73:7-12 (1988).
Deible et al., "Molecular barriers to biomaterial thrombosis by modification of surface proteins with polyethylene glycol," *Biomaterials*, 19:1885-1893 (1998).
De Venuto et al. "Rejuvenation of Human Red Blood Cells During Liquid Storage," *Transfusion*, 14(4):338-344 (1974).
Dumaswala et al., "Studies in Red Blood Cell Preservation: 9. The Role of Glutamine in Red Cell Preservation," *Vox Sang*, 67:255-259 (1994).
Dumaswala et al., "Glutamine- and Phosphate-Containing Hypotonic Storage Media Better Maintain Erythrocyte Membrane Physical Properties," *Blood*, 88(2):697-704 (1996).
Dumaswala et al., "Improved Red Blood Cell Preservation Correlates With Decreased Loss of Bands 3, 4.1, Acetylcholinestrase, and Lipids in Microvesicles," *Blood*, 87(4):1612-1616 (1996).
Dumont et al., "Anaerobic storage of red blood cells in a novel additive solution improves in vivo recovery," *Transfusion*, 49(3):458-464 (2009).
Effenhauser et al., "Integrated Capillary Electrophoresis on Flexible Silicone Microdevices: Analysis of DNA Restriction Fragments and Detection of Single DNA Molecules on Microchips," *Anal. Chem.*, 69:3451-3457 (1997).
European Search Report completed on Feb. 11, 2005, in European Patent Application No. 02 78 2307.9.
Fahraeus et al., "The Viscosity of the Blood in Narrow Capillary Tubes," *Am. J. Physiol.*, 96(3):562-568 (1931).
Fang et al., "Inhibition of Lipopolysaccharide-Associated Endotoxin Activities In Vitro and In Vivo by the Human Anti-Lipid A Monoclonal Antibody SdJ5-1.17.15," *Infection and Immunity*, 61(9):3873-3878 (1993).
Frame et al., "A System for Culture of Endothelial Cells in 20-50-µm Branching Tubes," *Microcirculation*, 2 (4):377-385 (1995).
Fung et al., "High-Resolution Data on the Geometry of Red Blood Cells", *Biorheology*, 18:369-385 (1981).
Gañán-Calvo et al., "Current and Droplet Size in the Electrospraying of Liquids. Scaling Laws," *J. Aerosol Sci.*, 28(2):249-275 (1997).
Green et al., "10. Liposomal Vaccines," Immunobiology of Proteins and Peptides VII, Plenum Press, New York, pp. 83-92 (1995).
Greenwalt et al., "Studies in Red Blood Cell Preservation. 7. In vivo and in Vitro Studies with a Modified Phosphate-Ammonium Additive Solution," *Vox Sang*, 65:87-94 (1993).
Greenwalt et al., "Studies in Red Blood Cell Preservation. 8. Liquid Storage of Red Cells in Glycerol-Containing Additive Solution," *Vox. Sang*, 67:139-143 (1994).
Greenwalt et al., "Studies in red blood cell preservation. 10. $^{51}$Cr Recovery of Red Cells after Liquid Storage in a Glycerol-Containing Additive Solution," *Vox Sang*, 70:6-10 (1996).
Greenwalt et al., "The effect of hypotonicity, glutamine, and glycine on red cell preservation," *Transfusion*, 37:269-276 (1997).
Griffith, "Temporal chaos in the microcirculation," *Cardiovascular Research*, 31:342-358 (1996).

Hamasaki et al., "Acid-citrate-dextrose-phosphoenolpyruvate medium as a rejuvenant for blood storage," *Transfusion*, 23(1):1-7 (1983).
Hess, "Extended Liquid Storage of Red Blood Cells," Blood Donors and the Supply of Blood and Blood Products, National Academy Press, Washington, D.C., pp. 99-102 (1996).
Hess et al., "Successful storage of RBCs for 9 weeks in a new additive solution," *Transfusion*, 40:1007-1011 (2000).
Hess, "Storage of red blood cells under anaerobic conditions," *Vox Sanguinis*, 93:183 (2007).
Hodgson et al., "Prophylactic use of human endotoxin-core hyperimmune gammaglobulin to prevent endotoxaemia in colostrum-deprived, gnotobiotic lambs challenged orally with *Escherichia coli*," *FEMS Immunology and Medical Microbiology*, 11:171-180 (1995).
Högman et al., "Cell Shape and Total Adenylate Concentration as Important Factors for Posttransfusion Survival of Erythrocytes," *Biomed. Biochim. Acta*, 42:S327-S331 (1983).
Högman et al.,"Effects of Oxygen on Red Cells during Liquid Storage at +4° C," *Vox Sang.*, 51:27-34 (1986).
Högman et al., "Effects of Oxygen and Mixing on red cells stored in plastic bags at +4° C," *Biomed. Biochim. Acta.*, 46:S290-S294 (1987).
Högman et al., "Shall Red Cell Units Stand Upright, Lie Flat or be Mixed During Storage? In Vitro Studies of Red Cells Collected in 0.5 CPD and Stored in RAS2 (Erythrosol®)," *Transfus. Sci.*, 16(2):193-199 (1995).
Huang et al., "Continuous Particle Separation Through Deterministic Lateral Displacement," *Science*, 304:987-990 (2004).
International Preliminary Report on Patentability completed on Feb. 14, 2012, in International Patent Application No. PCT/US2010/52084.
International Preliminary Report on Patentability completed on May 21, 2012, in International Patent Application No. PCT/US2010/52376.
International Preliminary Report on Patentability completed on Oct. 18, 2011, in International Patent Application No. PCT/US2010/031055.
International Search Report completed on Jul. 8, 1996, in International Patent Application No. PCT/US96/09005.
International Search Report completed on Nov. 10, 2003, in International Patent Application No. PCT/US02/36735.
International Search Report completed on May 20, 2010, in International Patent Application No. PCT/US2010/31055.
International Search Report completed on Apr. 26, 2011, in International Patent Application No. PCT/US2010/044045.
International Search Report completed on Dec. 21, 2011, in International Patent Application No. PCT/US11/49168.
International Search Report completed on Feb. 12, 2012, in International Patent Application No. PCT/US11/59372.
International Search Report completed on Jun. 18, 2012, in International Patent Application No. PCT/US12/30930.
International Search Report completed on Sep. 24, 2012, in International Patent Application No. PCT/US12/50380.
Jain, et al., "Determinants of Leukocyte Margination in Rectangular Microchannels," *PLoS ONE*, 4(9):1-8 (2009).
Jayasinghe et al., "Controlled deposition of nanoparticle clusters by electrohydrodynamic atomization," *Nanotechnology*, 15:1519-1523 (2004).
Jiang et al., "Microfluidic synthesis of monodisperse PDMS microbeads as discrete oxygen sensors," *Soft Matter*, 8:923-926 (2011).
Jo et al., "Surface modification using silanated poly(ethylene glycol)s," *Biomaterials*, 21:605-616 (2000).
Johnson et al., "Regulation of blood flow in single capillaries," *American Journal of Physiology*, 212:1405-1415 (1967).
Kaihara et al., "Silicon Micromachining to Tissue Engineer Branched Vascular Channels for Liver Fabrication," *Tissue Engineering*, 6(2):105-117 (2000).
Kiani et al., "Fluctuations in microvascular blood flow parameters caused by hemodynamic mechanisms," *American Journal of Physiology*, 266(5):H1822-H1828 (1994).

(56) References Cited

OTHER PUBLICATIONS

Kikuchi et al., "Modified Cell-Flow Microchannels in a Single-Crystal Silicon Substrate and Flow Behavior of Blood Cells," *Microvascular Research*, 47:126-139 (1994).
Koch et al., "Peripheral blood leukocyte NO production and oxidative stress in multiple sclerosis," *Multiple Sclerosis*, 14:159-165 (2008).
Koch et al., "Duration of Red-Cell Storage and Complications After Cardiac Surgery," *The New England Journal of Medicine*, 358:1229-1239 (2008).
Krogh, "Studies on the physiology of capillaries. II. The reactions to local stimuli of the blood-vessels in the skin and web of the frog," *The Journal of Physiology*, 55:412-422 (1921).
Kuraoka, et al., "Ship-in-a-bottle synthesis of a cobalt phthalocyanine/porous glass composite membrane for oxygen separation," *Journal of Membrane Science*, 286(1-2):12-14 (2006).
Lugowski et al., "Anti-endotoxin antibodies directed against *Escherichia coli* R-1 oligosaccharide core-tetanus toxoid conjugate bind to smooth, live bacteria and smooth lipopolysaccharides and attenuate their tumor necrosis factor stimulating activity," *FEMS Immunology and Medical Microbiology*, 16:31-38 (1996).
Mazor et al., "Prolonged Storage of Red Cells: The Effect of pH, Adenine Phosphate," *Vox Sanguinis*, 66:264-269 (1994).
McDonald et al., "Poly(dimethylsiloxane) as a Material for Fabricating Microfluidic Devices," *Accounts of Chemical Research*, 35(7):491-499 (2002).
Meryman et al., "Prolonged storage of red cells at 4° C," *Transfusion*, 26(6):500-505 (1986).
Meryman et al., "Extending the storage of red cells at 4° C," *Transfus. Sci.*, 15(2):105-115 (1994).
Moll et al., "Dean vortices applied to membrane process. Part II: Numerical approach," *Journal of Membrane Science*, 288:321-335 (2007).
Moroff et al., "Proposed standardization of methods for determining the 24-hour survival of stored red cells," *Transfusion*, 24:109-114 (1984).
Murphy et al., "Increased Mortality, Postoperative Morbidity, and Cost After Red Blood Cell Transfusion in Patients Having Cardiac Surgery," *Circulation*, 116:2544-2552 (2007).
Ng et al., "Components for integrated poly(dimethylsiloxane) microfluidic systems," *Electrophoresis*, 23:3461-3473 (2002).
Ohkuma et al., "The preservative-exchange method using a sextuple-bag system for a 10-week storage period of red blood cells," *Transfusion Medicine*, 1:257-262 (1991).
Poxton, "Antibodies to lipopolysaccharide," *Journal of Immunological Methods*, 186:1-15 (1995).
Pries et al., "Biophysical aspects of blood flow in the microvasculature," *Cardiovascular Research*, 32:654-667 (1996).
Sambuceti et al., "Why should we study the coronary microcirculation?," *Am J Physiol Heart Circ Physiol*, 279:H2581-H2584 (2000).
Shevkoplyas et al., "Direct measurement of the impact of impaired erythrocyte deformability on microvascular network perfusion in a microfluidic device," *Lab Chip*, 6:914-920 (2006).
Shimizu et al., "Multicenter Clinical Evaluation of Red Cell Concentrates Stored up to 6 Weeks in MAP, a new additive solution," *Japanese Journal of Clinical Hematology*, 33(2):148-156 (1992).
Skalak et al., "Deformation of Red Blood Cell in Capillaries," *Science*, 164(3880):717-719 (1969).
Sohmer et al., "Phosphoenolypyruvate (PEP) Effects on Fresh and Stored Red Blood Cells," *Proceedings of the Society for Experimental Biology and Medicine*, 171:24-33 (1982).
Sutton et al., "A Novel Instrument for Studying the Flow Behaviour of Erythrocytes through Microchannels Simulating Human Blood Capillaries," *Microvascular Research*, 53:272-281 (1997).
Szymanski et al., "Effect of rejuvenation and frozen storage on 42-day-old AS-1 RBCs," *Transfusion*, 41:550-555 (2001).
The International Committee for Standardization in Hematology, "Recommended Methods for Radioisotope Red Cell Survival Studies," *Blood*, 38(3):378-386 (1971).
Tinmouth et al., "The Clinical Consequences of the Red Cell Storage Lesion," *Transfusion Medicine Reviews*, 15(2):91-107 (2001).
Tracey et al., "A Silicon Micromachined Device for Use in Blood Cell Deformability Studies," *IEEE Transactions on Biomedical Engineering*, 42(8):751-761 (1995).
Tsukada et al., "Direct Measurement of Erythrocyte Deformability in Diabetes Mellitus with a Transparent Microchannel Capillary Model and High-Speed Video Camera System," *Microvascular Research*, 61:231-239 (2001).
Valeri et al., "The survival, function, and hemolysis of human RBCs stored at 4° C in additive solution (AS-1, AS-3, or AS-5) for 42 days and then biochemically modified, frozen, thawed, washed, and stored at 4° C in sodium chloride and glucose solution for 24 hours," *Transfusion*, 40:1341-1345 (2000).
Wang et al., "Fabrication of PLGA microvessel scaffolds with circular microchannels using soft lithography," *Journal of Micromechanics and Microengineering*, 17(10):2000-2005 (2007).
Weinberg et al., "Transfusions in the Less Severely injured: Does Age of Transfused Blood Affect Outcomes?," *The Journal of Trauma*, 65(4):794-798 (2008).
Wilding et al., "Manipulation and Flow of Biological Fuids in Straight Channels Micromachined in Silicon," *Clinical Chemistry*, 40(1):43-47 (1994).
Wood et al., "The Viability of Human Blood Stored in Phosphate Adenine Media," *Transfusion*, 7(6):401-408 (1967).
Wu et al., "Polymer microchips bonded by $O_2$-plasma activation," *Electrophoresis*, 23:782-790 (2002).
Yoshida et al., "Extended storage of red blood cells under anaerobic conditions," *Vox Sanguinis*, 92:22-31 (2007).
Yoshida et al., "Storage of red blood cells under anaerobic conditions: reply," *Vox Sanguinis*, 93:184 (2007).
Yoshida et al., "The effects of additive solution pH and metabolic rejuvenation on anaerobic storage of red cells," *Transfusion*, 48:2096-2105 (2008).
Yoshida et al., "Anaerobic storage of red blood cells," *Blood Transfus*, 8:220-236 (2010).
Zhang et al., "Modification of Si(100) surface by the grafting of poly(ethylene glycol) for reduction in protein adsorption and platelet adhesion," *J Biomed Mater Res*, 56:324-332 (2001).
Zimrin et al., "Current issues relating to the transfusion of stored red blood cells," *Vox Sanguinis*, 96:93-103 (2009).

\* cited by examiner

OXYGEN DEPLETION DEVICES AND METHODS FOR REMOVING OXYGEN FROM RED BLOOD CELLS

CROSS-REFERENCE TO RELATED APPLICATIONS

The present application is a Continuation application of U.S. patent application Ser. No. 12/903,057, filed on Oct. 12, 2010 now abandoned, which claims priority based on U.S. Provisional Application No. 61/250,661, filed Oct. 12, 2009, both of which are incorporated herein by reference in its entirety.

STATEMENT REGARDING FEDERALLY SPONSORED RESEARCH

This invention was made with government support under grants awarded by the National Institutes of Health (NIH) and the National Heart Lung and Blood Institute (NHLBI). The government has certain rights in the invention.

BACKGROUND OF THE INVENTION

1. Field of the Invention

The present invention relates to devices for depleting oxygen from red blood cells to enhance storage life. The present invention relates to methods for depleting oxygen from red blood cells.

2. Background of the Art

Adequate blood supply and the storage thereof is a problem facing every major hospital and health organization around the world. Often, the amount of blood supply in storage is considerably smaller than the need therefor. This is especially true during crisis periods such as natural catastrophes, war and the like, when the blood supply is often perilously close to running out. It is at critical times such as these that the cry for more donations of fresh blood is often heard. However, unfortunately, even when there is no crisis period, the blood supply and that kept in storage must be constantly monitored and replenished, because stored blood does not maintain its viability for long.

Stored blood undergoes steady deterioration which is, in part, caused by hemoglobin oxidation and degradation and adenosine triphosphate (ATP) and 2-3,biphosphoglycerate (DPG) depletion. Oxygen causes hemoglobin (Hb) carried by the red blood cells (RBCs) to convert to met-Hb, the breakdown of which produces toxic products such as hemichrome, hemin and free $Fe^{3+}$. Together with the oxygen, these products catalyze the formation of hydroxyl radicals (OH.cndot.), and both the OH.cndot. and the met-Hb breakdown products damage the red blood cell lipid membrane, the membrane skeleton, and the cell contents. As such, stored blood is considered unusable after 6 weeks, as determined by the relative inability of the red blood cells to survive in the circulation of the transfusion recipient. The depletion of DPG prevents adequate transport of oxygen to tissue thereby lowering the efficacy of transfusion immediately after administration (levels of DPG recover once in recipient after 8-48 hrs). In addition, these deleterious effects also result in reduced overall efficacy and increased side effects of transfusion therapy with stored blood before expiration date, but possibly older than two weeks are used.

There is, therefore, a need to be able to deplete oxygen levels in red blood cells prior to storage on a long-term basis without the stored blood undergoing the harmful effects caused by the oxygen and hemoglobin interaction.

SUMMARY OF THE INVENTION

Accordingly, the present disclosure provides for a disposable device that is able to remove oxygen from red blood cells.

The present disclosure provides for an oxygen depletion device. The device has a cartridge; a plurality of hollow fibers extending within the cartridge from an entrance to an exit thereof; an amount of an oxygen scavenger packed within the cartridge and contiguous to and in between the plurality of hollow fibers. The hollow fibers are adapted to receiving and conveying red blood cells.

The present disclosure provides for an oxygen depletion device. The device has a receptacle of a solid material having an inlet and an outlet adapted to receiving and expelling a flushing gas and a plurality of hollow fibers extending within the receptacle from an entrance to an exit thereof. The hollow fibers are adapted to receiving and conveying red blood cells.

The present disclosure provides for a method for removing oxygen from red blood cells. The method has the step of passing the red blood cells through an oxygen device. The device has a cartridge; a plurality of hollow fibers extending within the cartridge from an entrance to an exit thereof; and an amount of an oxygen scavenger packed within the cartridge and contiguous to and in between the plurality of hollow fibers. The hollow fibers are adapted to receiving and conveying red blood cells The present disclosure provides for a method for removing oxygen from red blood cells. The method has the step of passing the red blood cells through an oxygen device. The device has a receptacle of a solid material having an inlet and an outlet adapted to receiving and expelling a flushing gas; and a plurality of hollow fibers films extending within the receptacle from an entrance to an exit thereof. The hollow fibers are adapted to receiving and conveying red blood cells.

The present disclosure and its features and advantages will become more apparent from the following detailed description with reference to the accompanying drawings.

DETAILED DESCRIPTION OF THE DISCLOSURE

Figure 1:
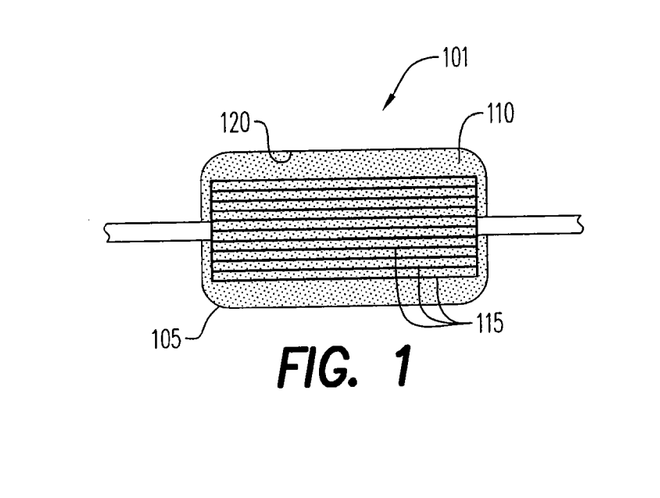
FIG. 1 illustrates a pre-storage oxygen depletion device of the present invention.
Figure 2A:
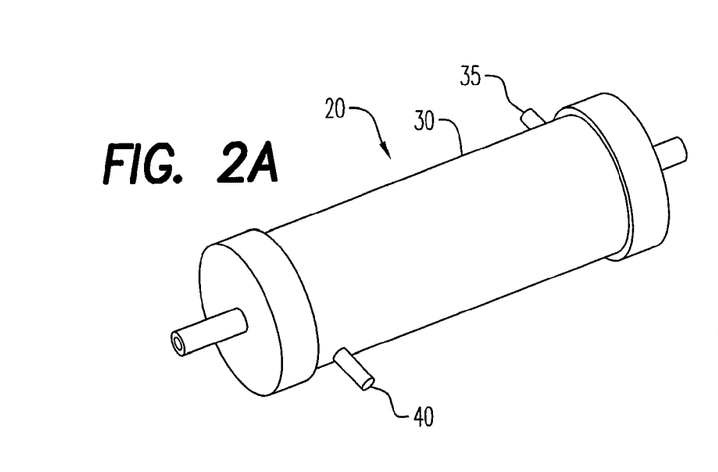
FIG. 2a illustrates an embodiment of a depletion device that depletes oxygen from red blood cells prior to storage by a flushing inert gas around a hollow fiber inside the assembly.
Figure 2B:
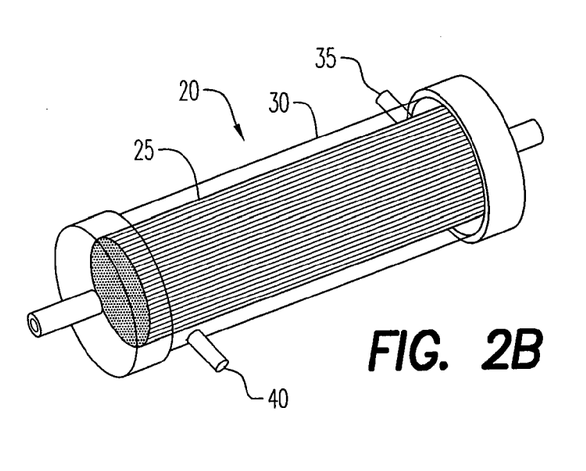
FIG. 2b illustrates an embodiment of a depletion device that depletes oxygen from red blood cells prior to storage by a flushing inert gas around a hollow fiber inside the assembly.
Figure 2C:
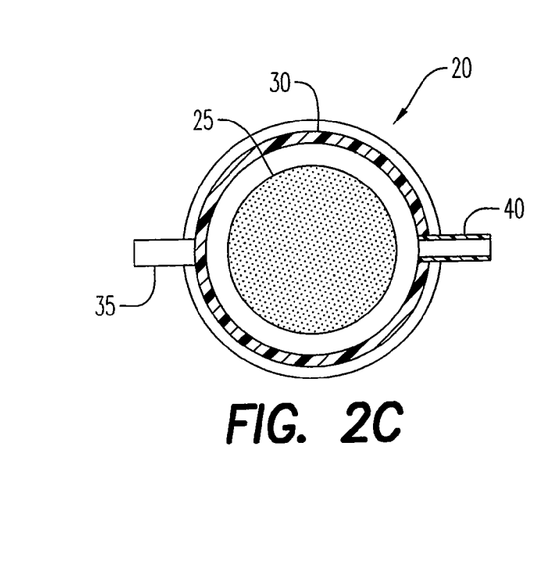
FIG. 2c illustrates an embodiment of a depletion device that depletes oxygen from red blood cells prior to storage by a flushing inert gas around a hollow fiber inside the assembly.

Referring to FIG. 2, an oxygen depletion device (ODD) 101 contains an oxygen sorbent 110. ODD 101 is a disposable cartridge 105 containing oxygen sorbent 110 and a series of hollow fibers 115. Oxygen sorbent 110 is a mixture of non-toxic inorganic and/or organic salts and ferrous iron or other materials with high reactivity toward oxygen. Oxygen sorbent 110 is made from particles that have significant absorbing capacity for $O_2$ (more than 5 ml $O_2$/g) and can maintain the inside of cartridge 105 to less than 0.01%, which corresponds to $PO_2$ less than 0.08 mmHg. Oxygen sorbent 110 is either free or contained in an oxygen permeable envelope. ODD 101 of the present disclosure can deplete approximately 100 mL of oxygen from a unit of blood.

RBCs pass through hollow porous fibers 115. Porous fibers are capable of high oxygen permeability rates. Suitable materials for porous fibers include polyolefins, TEFLON® (polytetrafluoroethylene), polyesters, polyvinylidene fluoride (PVDF), polysulfone, and other hydrophobic polymers as well as inorganic materials (ceramics). Oxygen depletion takes place as RBCs pass through membrane 115. ODD provides a simple structure having a large surface area to remove oxygen and maintain constant flow of blood therethrough. The oxygen depletion or removal is accomplished by irreversible reaction of ferrous ion in oxygen sorbent 110 with ambient oxygen to form ferric oxide. ODD 101 does not need agitation for oxygen removal and can be manufactured easily to withstand centrifugation as part of a blood collection system as necessary.

Referring to FIGS. 2a through 2c and FIGS. 3a through 3c, examples of flushing depletion devices are disclosed. The depletion devices function to deplete $O_2$ by supplying appropriate composition of flushing gas. Gases appropriate for depletion devices include, for example, Ar, He, $CO_2$, $N_2$.

FIGS. 4a through 4c and 5a through 5c, also disclose scavenging depletion devices. Depletion takes place with the use of scavengers or sorbents and without the use of external gases. In both types of depletion devices however, oxygen depletion is effective to enhance DPG and ATP, respectively, prior to storage in blood storage bags.

Referring to FIGS. 2a through 2c, a depletion device 20 is shown. Depletion device 20 includes a plurality of fibers 25, approximately 5000 in number, through which red blood cells flow. Plurality of fibers 25 are surrounded by a plastic cylinder 30. Plastic cylinder 30 contains a gas inlet 35 and a gas outlet 40 through which a flushing gas or a combination of flushing gases, such as those mentioned above, are supplied to remove oxygen from blood. Specifications for depletion device 20 are shown in Table 1 below.

TABLE 1

| Prototype Specification | Eternal Gas Pathways | External Gas Pathways |
|---|---|---|
| Prototype Serial #: | Device 20 | |
| Fiber Type: | Celgard 200/150-66FPI | Celgard 200/150-66FPI |
| Number of Fibers: | 5000 | 5000 |
| Active Length of Fibers (cm): | 13 | 28 |
| Fiber OD (microns): | 200 | 200 |
| Fiber ID (microns): | 150 | 150 |
| Total Length of Fibers: | 15 | 30 |
| Active Fiber Surface Area (m2): | 0.4084 | 0.8796 |

Figures 3A, 3B, 3C:
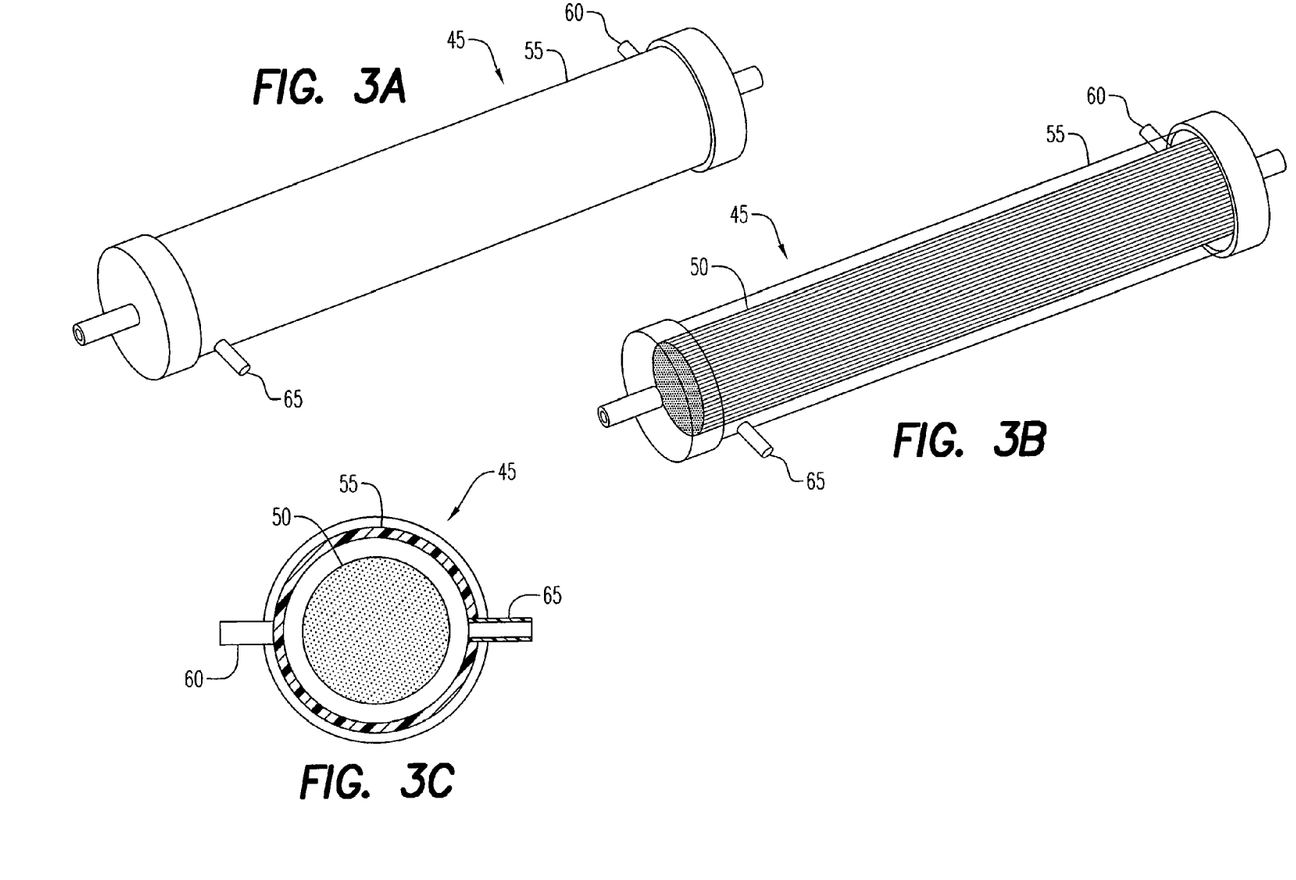
FIG. 3a illustrates another embodiment of a depletion device that depletes oxygen from red blood cells prior to storage.
FIG. 3b illustrates another embodiment of a depletion device that depletes oxygen from red blood cells prior to storage.
FIG. 3c illustrates another embodiment of a depletion device that depletes oxygen from red blood cells prior to storage.

Referring to FIGS. 3a through 3c, a depletion device 45 is shown. Depletion device 45, like device 20 of FIGS. 2a to 2c, includes a plurality of fibers 50, approximately 5000 in number, through which red blood cells flow. Plurality of fibers 50 are surrounded by a plastic cylinder 55. Plastic cylinder 55 contains a gas inlet 60 and a gas outlet 65 through which a gas or a combination of gases, such as those mentioned above are supplied to remove oxygen from blood. Specifications for depletion device 45 are shown in Table 2 below. The active surface area of depletion of device 45 is twice that of device 20 because device 45 is twice as long as device 20.

TABLE 2

| Prototype Specification | Eternal Gas Pathways | External Gas Pathways |
|---|---|---|
| Prototype Serial #: | | Device 45 |
| Fiber Type: | Celgard 200/150-66FPI | Celgard 200/150-66FPI |
| Number of Fibers: | 5000 | 5000 |
| Active Length of Fibers (cm): | 13 | 28 |
| Fiber OD (microns): | 200 | 200 |
| Fiber ID (microns): | 150 | 150 |
| Total Length of Fibers: | 15 | 30 |
| Active Fiber Surface Area (m2): | 0.4084 | 0.8796 |

Figures 4A, 4B, 4C:
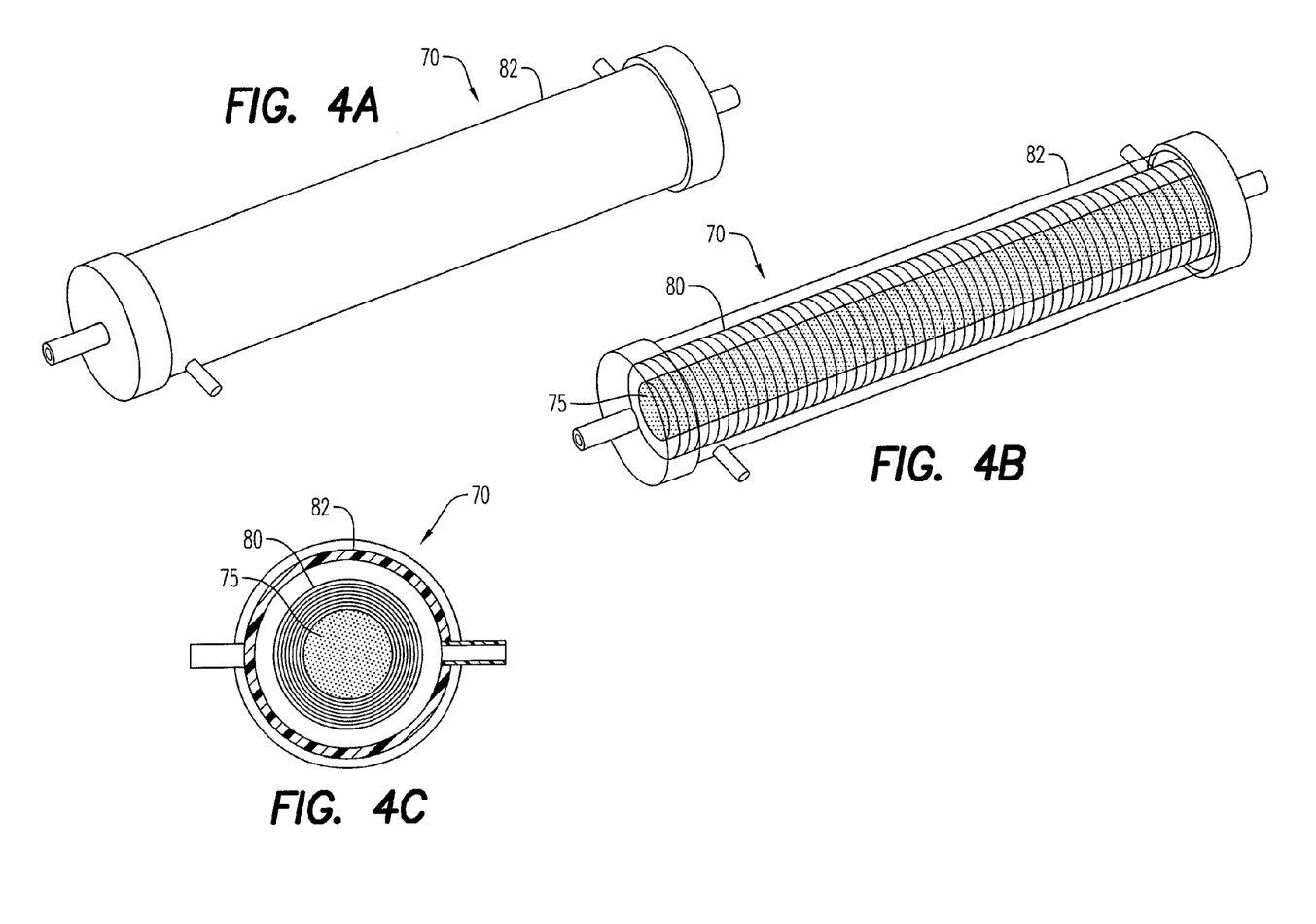
FIG. 4a illustrates another embodiment of a depletion device that depletes oxygen from red blood cells prior to storage wherein oxygen is scavenged by scavenger materials in the core of the cylinder, surrounded by hollow fibers.
FIG. 4b illustrates another embodiment of a depletion device that depletes oxygen from red blood cells prior to storage wherein oxygen is scavenged by scavenger materials in the core of the cylinder, surrounded by hollow fibers.
FIG. 4c illustrates another embodiment of a depletion device that depletes oxygen from red blood cells prior to storage wherein oxygen is scavenged by scavenger materials in the core of the cylinder, surrounded by hollow fibers.

FIGS. 4a through 4c disclose a depletion device 70 having a core 75 containing scavenging materials for $O_2$. Core 75 is packed by a gas permeable film with very low liquid permeability. Hollow fibers 80 are wound around core 75, and a plastic cylinder 82 contains and envelopes hollow fibers 80. In this particular embodiment, the active surface area for depletion is approximately 0.8796 $m^2$ as shown in Table 3 below.

TABLE 3

| Prototype Specification | Center Core 125 grams Sorbent | 10 individual Bundles 200 grams Sorbent |
|---|---|---|
| Prototype Serial #: | Device 70 | |
| Fiber Type: | Celgard 200/150-66FPI | Celgard 200/150-66FPI |
| Number of Fibers: | 5000 | 5000 |
| Active Length of Fibers (cm): | 13 | 28 |
| Fiber OD (microns): | 200 | 200 |

TABLE 3-continued

| Prototype Specification | Center Core 125 grams Sorbent | 10 individual Bundles 200 grams Sorbent |
|---|---|---|
| Fiber ID (microns): | 150 | 150 |
| Total Length of Fibers | 15 | 30 |
| Active Fiber Surface Area (m2): | 0.8796 | 0.8796 |

Figures 5A, 5B, 5C:
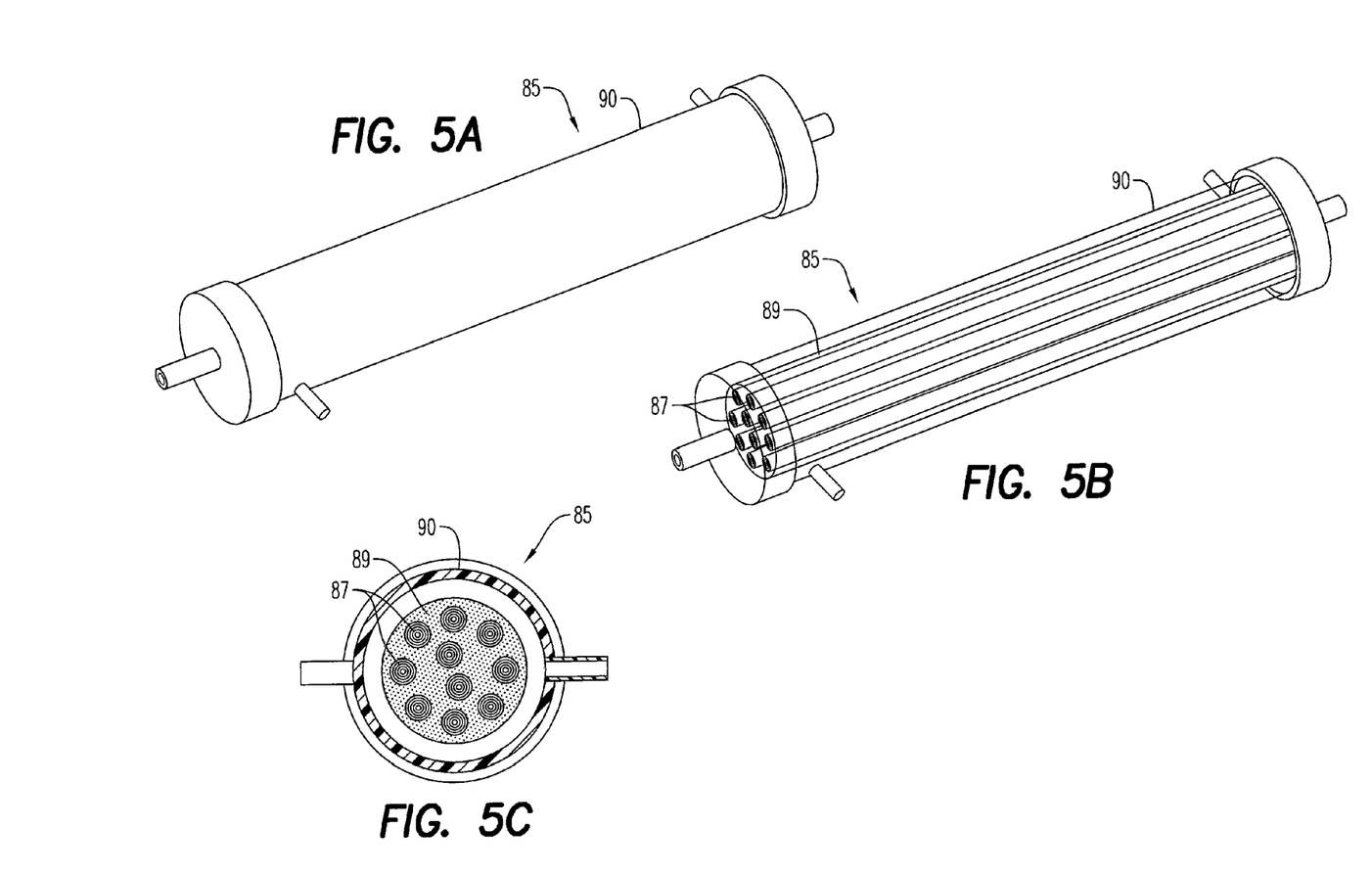
FIG. 5a illustrates another embodiment of a depletion device that depletes oxygen from red blood cells wherein oxygen is scavenged by scavenger materials surrounding cylinders of hollow fibers.
FIG. 5b illustrates another embodiment of a depletion device that depletes oxygen from red blood cells wherein oxygen is scavenged by scavenger materials surrounding cylinders of hollow fibers.
FIG. 5c illustrates another embodiment of a depletion device that depletes oxygen from red blood cells wherein oxygen is scavenged by scavenger materials surrounding cylinders of hollow fibers.

FIGS. 5a through 5c disclose a depletion device 85 containing fiber bundles 87 enclosed in gas permeable film with very low liquid permeability. Fiber bundles 87 are surrounded by scavenger materials 89 for $O_2$. Fiber bundles 87 and scavenger materials 89 are contained within a plastic cylinder 90. The active surface area for depletion is approximately 0.8796 $m^2$ as shown in Table 4 below.

TABLE 4

| Prototype Specification | Center Core 125 grams Sorbent | 10 individual Bundles 200 grams Sorbent |
|---|---|---|
| Prototype Serial #: | | Device 85 |
| Fiber Type: | Celgard 200/150-66FPI | Celgard 200/150-66FPI |
| Number of Fibers: | 5000 | 5000 |
| Active Length of Fibers (cm): | 13 | 28 |
| Fiber OD (microns): | 200 | 200 |
| Fiber ID (microns): | 150 | 150 |
| Total Length of Fibers | 15 | 30 |
| Active Fiber Surface Area ($m^2$): | 0.8796 | 0.8796 |

Figure 6:
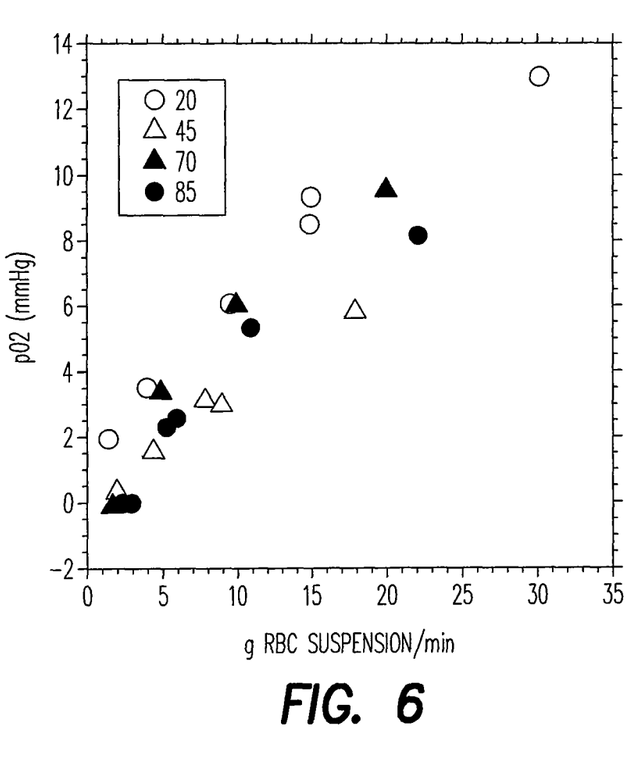
FIG. 6 illustrates a plot of flow rate of RBC suspension per minute versus oxygen partial pressure for the depletion devices of FIGS. 2a through 2c, FIGS. 3a through 3c, FIGS. 4a through 4c and FIGS. 5a through 5c.

FIG. 6 is a plot of the performance of flushing depletion devices 20 and 45 and scavenging depletion devices 70 and 85. The data of FIG. 6 was plotted using the following conditions: Hematocrit, 62% (pooled 3 units of pRBC), and 21° C. at various head heights to produce different flow rates. Oxygen scavenger (Multisorb Technologies, Buffalo, N.Y.) was activated with adding 5% and 12% w/w water vapor for device 79 and device 85, respectively. Data are plotted with flow rate (g RBC suspension per min) vs. $pO_2$ (mmHg).

In the oxygen depletion devices disclosed herein, the hollow fibers may be packed in any suitable configuration within the cartridge, such as linear or longitudinal, spiral, or coil, so long as they can receive and convey red blood cells.

FIG. 6 shows that lowest oxygen saturation is achieved using devices 45 and 85. Device 45 exhibits a larger active surface area exposed to gases along length of fibers 50. Device 85 also has a long surface area of exposure to scavenging materials. Device 85 has bundles 87 surrounded by scavenging materials 89. The space occupied by scavenging materials 89 between bundles 87 promotes dispersion of oxygen from red blood cells contained in fiber bundles 87, thus aiding scavenging of oxygen from red blood cells.

A further use of the depletion devices is to add back oxygen prior to transfusion by flushing with pure oxygen or air. This use is for special cases, such as massive transfusions, where the capacity of the lung to reoxygenate transfused blood is not adequate, or sickle cell anemia.

Similarly, depletion devices can be used to obtain intermediate levels or states of depletion of oxygen depending needs of the patient to obtain optimal levels in the transfused blood depending upon the patients needs.

It is within the scope of the present invention to remove oxygen from the RBCs or to strip oxygen from the blood prior to storage in the storage bags. An oxygen scavenger can be used to remove the oxygen from the RBCs prior to storage in the blood bags. As used herein, "oxygen scavenger" is a material that irreversibly binds to or combines with oxygen under the conditions of use. For example, the oxygen can chemically react with some component of the material and be converted into another compound. Any material where the off-rate of bound oxygen is zero can serve as an oxygen scavenger. Examples of oxygen scavengers include iron powders and organic compounds. The term "oxygen sorbent" may be used interchangeably herein with oxygen scavenger. For example, oxygen scavengers are provided by Multisorb Technologies (Buffalo, N.Y.). Such materials can be blended to a desired ratio to achieve desired results.

It will be appreciated that scavengers can be incorporated into storage receptacles and bags in any known form, such as in sachets, patches, coatings, pockets, and packets.

Although the present invention describes in detail certain embodiments, it is understood that variations and modifications exist known to those skilled in the art that are within the invention. Accordingly, the present invention is intended to encompass all such alternatives, modifications and variations that are within the scope of the invention as set forth in the disclosure.

What is claimed is:

1. An oxygen depletion device comprising:
 a cartridge;
 a plurality of hollow fibers extending within said cartridge from an entrance to an exit thereof, wherein the hollow fibers are formed of an oxygen-permeable membrane and are adapted to receiving and conveying red blood cells; and
 an amount of an oxygen scavenger packed within the cartridge and contiguous to and in between the plurality of hollow fibers, wherein said red blood cells are passaged within said hollow fibers.

2. The device of claim 1, wherein said hollow fibers are substantially parallel and longitudinally disposed within the cartridge from said entrance to said exit.

3. The oxygen depletion device of claim 1, wherein said oxygen scavenger is ferrous iron.

4. The oxygen depletion device of claim 1, wherein said plurality of hollow fibers are formed from an oxygen-permeable material selected from the group consisting of polyolefin, polytetrafluoroethylene, polyester, polvvinylidene fluoride (PVDF), and polysulfone.

5. The oxygen depletion device of claim 1, wherein said plurality of hollow fibers are formed from a hydrophobic polymer.

6. The oxygen depletion device of claim 1, wherein said plurality of hollow fibers are formed from an inorganic ceramic.

7. The oxygen depletion device of claim 1, wherein said plurality of hollow fibers are configured as a linear spiral, a longitudinal spiral, or a coil.

8. An oxygen depletion device comprising:
 a receptacle of a solid material having an inlet and an outlet adapted to receiving and expelling a flushing gas;
 a plurality of hollow fibers extending within the receptacle from an entrance to an exit thereof; wherein the hollow fibers are adapted to receiving and conveying red blood cells, wherein said red blood cells are passaged within said hollow fibers.

9. The device of claim 8, wherein the hollow fibers are substantially parallel and longitudinally disposed within the cartridge from said entrance to said exit.

10. The device of claim 8, further including a source of flushing gas in communication with said inlet of said receptacle.

11. A method for removing oxygen from red blood cells comprising:
 passing red blood cells through an oxygen depletion device, wherein the device comprises:
 a cartridge;
 a plurality of hollow fibers extending within said cartridge from an entrance to an exit thereof, wherein said plurality of hollow fibers are adapted to receiving and conveying red blood cells; and
 an amount of an oxygen scavenger packed within said cartridge and contiguous to and in between said plurality of hollow fibers, wherein said red blood cells are passaged within said hollow fibers.

12. The method of claim 11, wherein said oxygen scavenger is ferrous iron.

13. The method of claim 11, wherein said plurality of hollow fibers are formed from an oxygen-permeable material selected from the group consisting of polyolefin, polytetrafluoroethylene, polyester, polyvinylidene fluoride (PVDF), and polysulfone.

14. The method of claim 11, wherein said plurality of hollow fibers are formed from a hydrophobic polymer.

15. The method of claim 11, wherein said plurality of hollow fibers are formed from an inorganic ceramic.

16. The method of claim 11, wherein said plurality of hollow fibers are configured as a linear spiral, a longitudinal spiral, or a coil.

17. A method for removing oxygen from red blood cells comprising:
 passing the red blood cells through an oxygen depletion device, wherein the device comprises:
 a receptacle of a solid material having an inlet and an outlet adapted to receiving and expelling a flushing gas;
 a plurality of hollow fibers extending within the receptacle from an entrance to an exit thereof, wherein the hollow fibers are adapted to receiving and conveying red blood cells, wherein said red blood cells are passaged within said hollow fibers.

* * * * *

UNITED STATES PATENT AND TRADEMARK OFFICE
CERTIFICATE OF CORRECTION

PATENT NO. : 8,569,052 B2
APPLICATION NO. : 13/115532
DATED : October 29, 2013
INVENTOR(S) : William J. Federspiel et al.

Page 1 of 1

It is certified that error appears in the above-identified patent and that said Letters Patent is hereby corrected as shown below:

In the Claims:

Col. 6, line 43, Claim 4, "polvvinylidene" should read as --polyvinylidene--; and Col. 7, line 19, Claim 13, "polvvinylidene" should read as --polyvinylidene--.

Signed and Sealed this
Eleventh Day of February, 2014

Michelle K. Lee
*Deputy Director of the United States Patent and Trademark Office*